United States Patent [19]

Koda et al.

[11] 4,095,457
[45] Jun. 20, 1978

[54] APPARATUS FOR DETECTING CHANGES IN PARAMETERS OF LIQUID FLOWING IN A PIPE BASED ON SING-AROUND METHOD

[75] Inventors: Kazuo Koda; Masato Tsuchiya, both of Yokohama, Japan

[73] Assignee: Nippon Kokan Kabushiki Kaisha, Tokyo, Japan

[21] Appl. No.: 808,597

[22] Filed: Jun. 21, 1977

[30] Foreign Application Priority Data

Jul. 16, 1976 Japan .................................. 51-83943

[51] Int. Cl.² .......................................... G01N 29/02
[52] U.S. Cl. ........................................ 73/53; 73/597
[58] Field of Search ............ 73/32, 53, 67.5 R, 194 A, 73/560

[56] References Cited

U.S. PATENT DOCUMENTS

| 3,028,749 | 4/1962 | Welkowitz ................................. 73/32 |
| 3,100,885 | 8/1963 | Welkowitz et al. ................... 73/32 X |
| 3,715,709 | 2/1973 | Zacharias, Jr. et al. ........... 73/560 X |

*Primary Examiner*—Charles A. Ruehl
*Attorney, Agent, or Firm*—Flynn & Frishauf

[57] ABSTRACT

Apparatus for detecting changes in parameters of a liquid flowing in a pipe based on the sing-around method, comprises: a set of a transmitting probe and a receiving probe arranged opposite to each other on the outer surface of a pipe for transmitting and receiving an ultrasonic pulse; a masking circuit for transmitting a masking signal in response to a signal from said receiving probe; a one-shot pulse generator circuit for transmitting a pulse in response to said masking signal from said masking circuit; a masking time setup circuit for setting up a masking time of said masking signal of said masking circuit; a receiving monitor-time setup circuit and a pseudo-pulse generator circuit for transmitting a pseudo-pulse; a voltage/power converter circuit for converting said pulse from said one-shot pulse generator circuit into a power signal; and an output section for taking out said pulse from said one-shot pulse generator circuit as an output.

6 Claims, 14 Drawing Figures

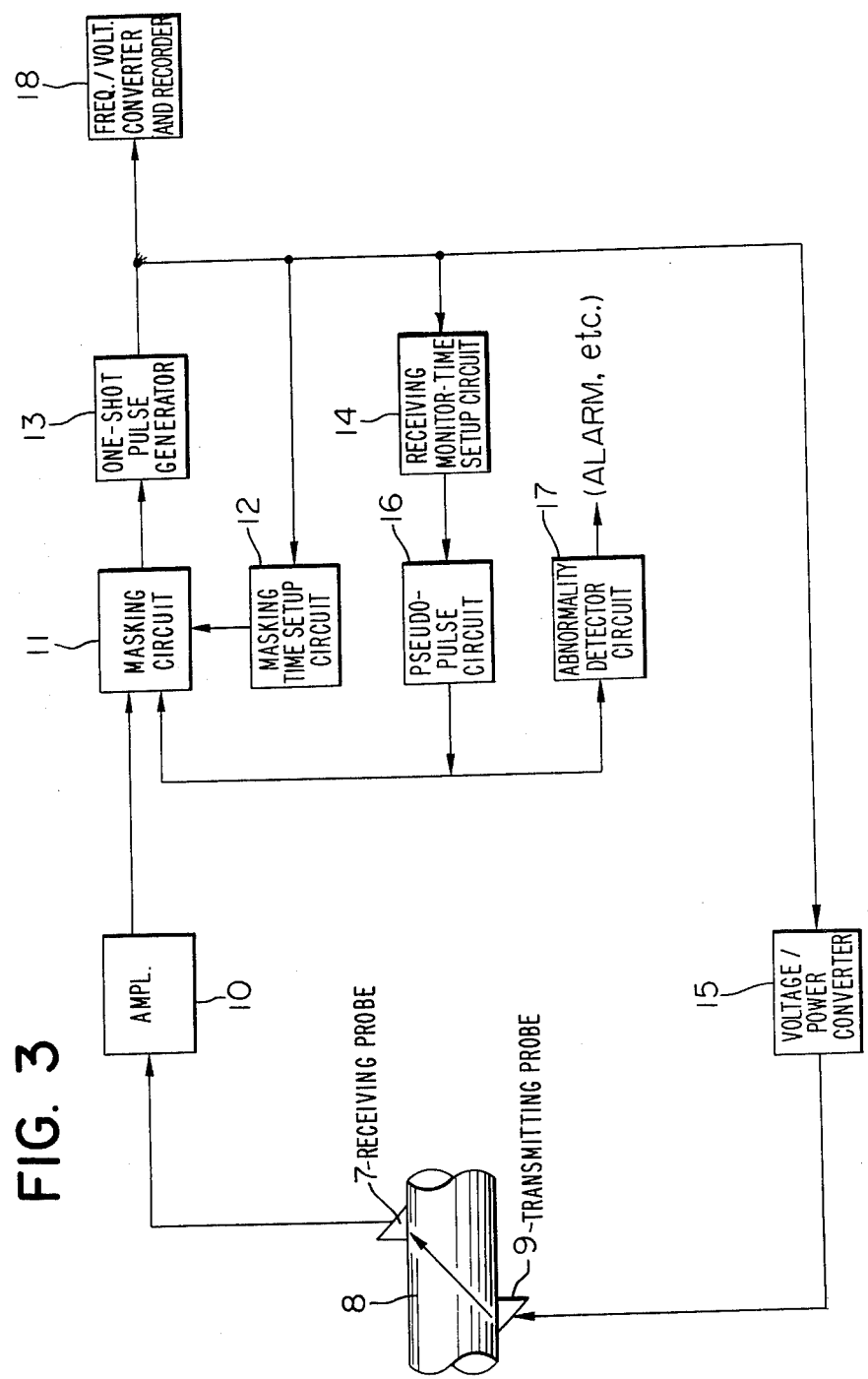

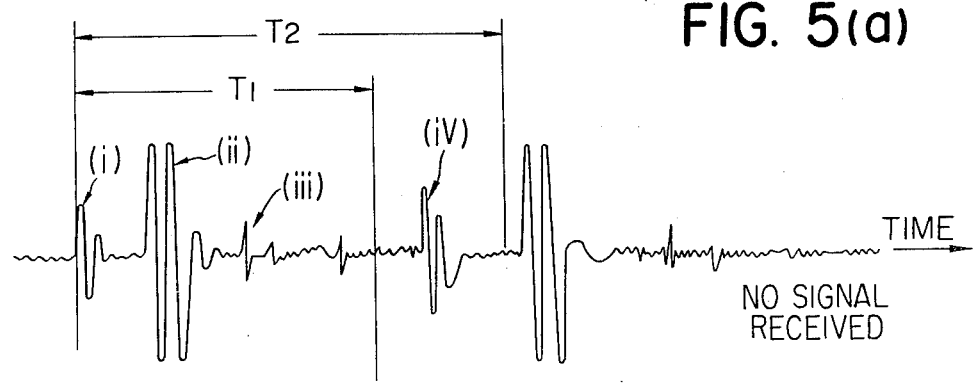
FIG. 5(a)
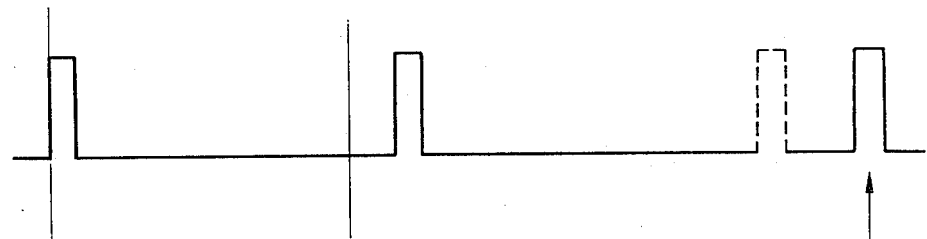
FIG. 5(b)
FIG. 5(c)
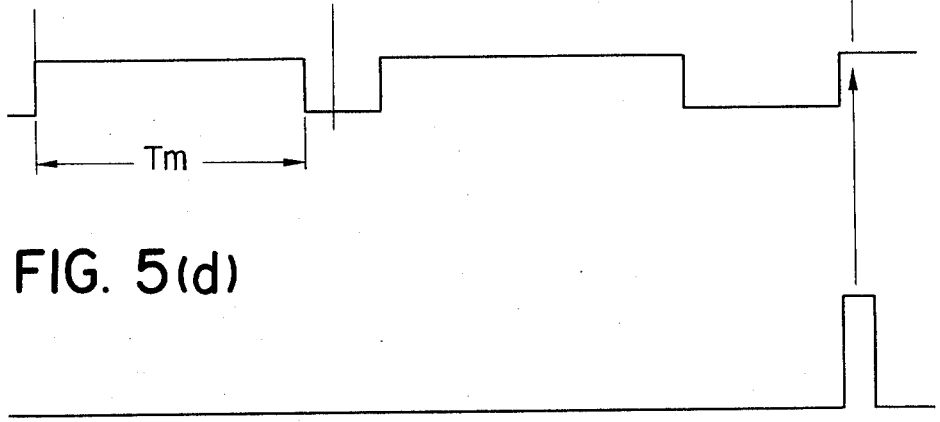
FIG. 5(d)

APPARATUS FOR DETECTING CHANGES IN PARAMETERS OF LIQUID FLOWING IN A PIPE BASED ON SING-AROUND METHOD

FIELD OF THE INVENTION

The present invention relates to an apparatus for detecting changes in parameters of a liquid flowing in a pipe, such as the density, the bulk modulus, the concentration and the temperature, which is based on the sing-around method.

BACKGROUND OF THE INVENTION

In liquid transportation through a pipeline to a destination, in general, it is often a usual practice to transport different liquids simultaneously through a single pipeline with a view to effectively utilizing the pipeline. It is necessary in this case to accurately detect the boundary between different liquids flowing in the pipeline from outside the pipeline at the destination and to separate a liquid from the others by switching over the route of the pipeline at said boundary.

There are several methods available for detecting from outside the pipeline the boundary between different liquids flowing in a pipeline. Among others, a method for detecting said boundary based on the sing-around method is known, which employs the fact that the sound velocity varies with the change in the natural physical properties of a medium such as the density and the bulk modulus.

The sing-around method, which permits continuous measurement of the velocity of an ultrasonic wave, is based on the following principle: fixing a transmitting probe and a receiving probe at a certain distance; emitting an ultrasonic pulse from the transmitting probe into a liquid in response to a voltage signal from a pulse oscillator; receiving said ultrasonic pulse by the receiving probe; converting said received pulse into a voltage signal; subjecting said voltage signal to an amplification and a wave-forming; starting up again the pulse oscillator with the thus processed voltage signal to emit an ultrasonic pulse again from the transmitting probe into the liquid; thus repeatedly emitting an ultrasonic pulse from the transmitting probe within a closed loop; counting the frequency of repetition of the ultrasonic pulse (hereinafter referred to as "sing-around frequency") on these repeated emissions with a frequency counter; and calculating the sound velocity through the liquid in accordance with the following equation:

$$1/f = l/c$$

where,
 $l$: distance between transmitting and receiving probes,
 $c$: sound velocity through the liquid, and
 $f$: sing-around frequency.

The time lag in the electric circuit, which should be taken into account in the above-mentioned equation, is omitted here for simplification of description.

FIG. 1 is a drawing schematically illustrating the conventional apparatus for detecting the boundary between different liquids flowing in a pipeline, based on the above-mentioned sing-around method. For the purpose of preventing multiple reflection of an ultrasonic pulse, as shown in this drawing, a transmitting probe 2 and a receiving probe 3 are provided on the outer surface of a pipeline 4 at an angle therewith, so that an ultrasonic pulse may be emitted at said angle with the flow direction of the liquid in the pipeline 4 (indicated by an arrow in the drawing). An ultrasonic pulse is repeatedly emitted from the transmitting probe 2 into the liquid as described above. The sing-around frequency is converted into a voltage output by a frequency/voltage converter 5, and said voltage output is recorded in a recorder 6. In FIG. 1, 1 indicates a sing-around circuit. A change in the density of liquid flowing in the pipeline 4, that is, the passage of a boundary between different liquids across a given point, leads to a change in the sing-around frequency, and hence to a change in the voltage output. It is thus possible to detect the boundary between different liquids from outside the pipe 4.

In the above-mentioned conventional sing-around circuit which employs an external forced synchronizing astable multivibrator (hereafter referred to as "astable multivibrator") as the pulse oscillator, the frequency of a transmission pulse of the astable multivibrator is synchronized with the frequency of a signal from the receiving probe, and the resulting synchronized transmission pulse is used as a transmission signal.

In a free state in which an external forced synchronizing signal (hereafter referred to as "synchronizing signal") is not given as a trigger signal, the astable multivibrator emits pulses in succession with a preset frequency and pulse width as shown in FIG. 2 (a). A synchronizing signal, if supplied during the on-state of the transmission pulse, causes no response of said transmission pulse to said synchronizing signal, whereas, during the off-state of said transmission pulse, said transmission pulse responds to a synchronizing signal, if it is supplied.

More specifically, if a synchronizing signal having a frequency slightly higher than that of the transmission pulse, as shown in FIG. 2 (b) or FIG. 2 (d), is supplied during the off-state of the transmission pulse of the astable multivibrator, the frequency of said transmission pulse is locked to the frequency of said synchronizing signal and synchronized therewith. The astable multivibrator emits accordingly a pulse with a frequency equal to that of said synchronizing signal and with its own pulse width, as shown in FIG. 2 (c) or FIG. 2 (e). On the contrary, when a synchronizing signal as shown in FIG. 2 (f) is supplied during the on-state of the transmission pulse of the astable multivibrator, said transmission pulse shows no response to said synchronizing signal, and hence, the astable multivibrator emits a pulse, as shown in FIG. 2 (g), with the same preset frequency and pulse width as those shown in FIG. 2 (a).

The boundary between different liquids flowing in a pipe has conventionally been detected with the use of the above-mentioned characteristic of the astable multivibrator. This conventional method has more specifically comprised setting the frequency of transmission pulse of an astable multivibrator at a value slightly lower than the sing-around frequency corresponding to a liquid flowing in a pipe giving the lowest sound velocity, and synchronizing the frequency of transmission pulse of said astable multivibrator with the sing-around frequency, i.e., with the frequency of a signal from a receiving probe, thereby using the thus synchronized transmission pulse as the transmission signal. An erroneous detection caused by noise has been prevented by masking received noise waves such as ultrasonic waves propagating along a pipe wall through adjustment of the pulse width of the transmission pulse of said astable multivibrator to a slightly wider width.

However, when employing an astable multivibrator in a sing-around circuit, it is inevitable that the following difficulties are encountered:

(1) When alteration of the kinds of liquids flowing in a pipe has caused a change in the sing-around frequency, the preset frequency of a transmission pulse of the astable multivibrator may exceed the limit of synchronization thereof with said sing-around frequency, i.e., with the frequency of a pulse from the receiving probe, depending upon the extent of the preset value of the frequency of the transmission pulse of said astable multivibrator itself, thus giving rise to the fear of impossibility of synchronization.

(2) When a ultrasonic pulse from the transmitting probe has not reached the receiving probe in a normal manner under the effect of air bubbles or foreign matters entangled into liquids flowing in a pipe, an erroneous detection may be caused unless instruments are carefully watched.

(3) The frequency and the pulse width of the transmission pulse of the astable multivibrator itself cannot be independently adjusted. It is therefore practically very difficult to adjust said pulse width to a larger desired value with a view to masking noise such as ultrasonic waves propagating along a pipe wall.

(4) When the astable multivibrator is used for a pipe of a different diameter, it is necessary to adjust the frequency and the pulse width of the transmission pulse thereof to values suitable for the diameter of the new pipe. It is however very difficult to make such an adjustment as mentioned above, and in particular, it is impossible to make such a site adjustment.

For these reasons, there has been a demand for an apparatus for detecting a change in paramenters of a liquid flowing in a pipe based on the sing-around method, which is free from the troubles mentioned above, but such an apparatus has not as yet been proposed.

SUMMARY OF THE INVENTION

An object of the present invention is therefore to provide an apparatus for detecting a change in parameters of a liquid flowing in a pipe based on the sing-around method, which permits substantial elimination of adverse effects due to received noise waves.

Another object of the present invention is to provide an apparatus for detecting a change in parameters of a liquid flowing in a pipe based on the sing-around method, which, even when a normal sing-around actuation is interrupted by some cause or other, permits immediate recovery thereof.

Still another object of the present invention is to provide an apparatus for detecting a change in parameters of a liquid flowing in a pipe based on the sing-around method, which, for a pipe of a different diameter, is applicable by a simple adjustment.

In accordance with one of the features of the present invention, there is provided an apparatus for detecting a change in parameters of a liquid flowing in a pipe based on the sing-around method, comprising:

a set of a transmitting probe and a receiving probe arranged opposite to each other on the outer surface of a pipe, said transmitting probe emitting an ultrasonic pulse through a liquid flowing in said pipe to said receiving probe, and said receiving probe converting said ultrasonic pulse from said transmitting probe into a voltage signal and transmitting said voltage signal;

an amplifier for amplifying said voltage signal from said receiving probe;

a masking circuit for transmitting a masking signal in response to said signal from said receiving probe as amplified by said amplifier, said masking circuit masking, during a preset masking time, noise signals other than normal ones from among signals from said receiving probe;

a one-shot pulse generator circuit for transmitting a pulse in response to said masking signal from said masking circuit;

a masking time setup circuit for setting up said masking time, said masking time setup circuit beginning actuation immediately upon resetting of a timer thereof in response to said pulse from said one-shot pulse generator circuit, and releasing said masking by said masking circuit by transmitting a masking release signal to said masking circuit at the moment when said masking time has elapsed, and said masking time being set up at a desired value by said timer within a range of periods slightly smaller than the sing-around period corresponding to a liquid flowing in said pipe giving the highest sound velocity and sufficient to permit masking of said noise signals;

a receiving monitor-time setup circuit for setting up a receiving monitor time during which interruptions of pulses transmitted from said on-shot pulse generator circuit are monitored, said receiving monitor-time setup circuit beginning actuation immediately upon resetting of a timer thereof in response to said pulse from said one-shot pulse generator circuit, and transmitting a signal when said timer has not been reset again by the next pulse from said one-shot pulse generator circuit during said receiving monitor time, and said receiving monitor time being setup by said timer at a desired value slightly larger than the sing-around period corresponding to a liquid flowing in said pipe giving the lowest sound velocity;

a pseudo-pulse generator circuit for transmitting a pseudo-pulse to said masking circuit in response to said signal from said receiving monitor-time setup circuit, said pseudo-pulse, like said signal from said receiving probe, causing said masking circuit to transmit a masking signal in response to said pseudo-pulse;

a voltage/power converter circuit for converting said pulse from said one-shot pulse generator circuit into a power signal and transmitting said power signal to said transmitting probe, said transmitting probe transmitting the next ultrasonic pulse in response to said power signal, and thus the sing-around actuation being continued; and an output section for taking out a pulse from said one-shot pulse generator circuit, i.e., the sing-around frequency, as an output, said output section comprising a frequency-voltage converter circuit and a recorder.

BRIEF DESCRIPTION OF THE DRAWING

FIG. 3 is a block diagram illustrating an embodiment of the apparatus for detecting a change in parameters of a liquid flowing in a pipe based on the sing-around method, of the present invention;

FIG. 5 (a) to FIG. 5 (d) are graphs illustrating the relation between a receiving signal and a transmission signal of the principal circuits in the apparatus of the present invention, wherein FIG. 5 (a) illustrates a signal transmitted from the receiving probe, FIG. 5 (b) illustrates a pulse transmitted from the one-shot pulse generator circuit, FIG. 5 (c) illustrates a masking signal transmitted from the masking circuit, and FIG. 5 (d) illustrates a pseudo-pulse transmitted from the pseudo-pulse generator circuit.

DETAILED DESCRIPTION OF PREFERRED EMBODIMENTS

Figure 1:
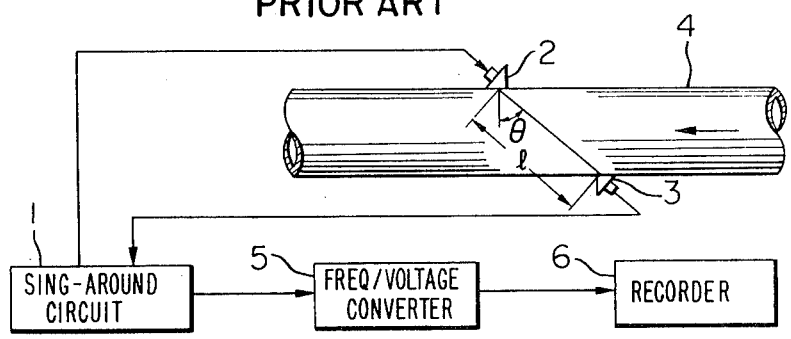
FIG. 1 is a schematic drawing illustrating a conventional apparatus for detecting the boundary between different liquids flowing in a pipe based on the sing-around method.
Figure 2A:
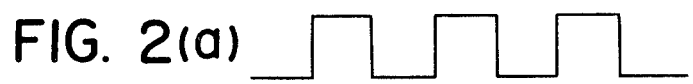
FIG. 2 (a) to FIG. 2 (g) are graphs illustrating the relation between an external forced synchronizing signal and a transmission signal of an astable multivibrator in said astable multivibrator used in the sing-around circuit of said conventional apparatus for detecting the boundary, wherein FIG. 2 (a) and FIG. 2 (g) illustrate a transmission pulse having preset frequency and pulse width, of said astable multivibrator, FIG. 2 (b), FIG. 2 (d) and FIG. 2 (f) illustrate said synchronizing signal, and FIG. 2 (c) and FIG. 2 (e) illustrate a transmission pulse of said astable multivibrator, synchronized with the frequency of said synchronizing signal.
Figure 2B:
Figure 2C:
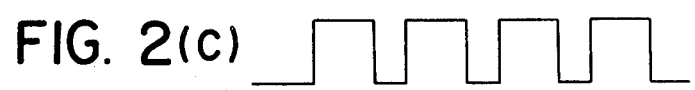
Figure 2D:
Figure 2E:
Figure 2F:
Figure 2G:

With a view to solving the aforementioned problems involved in the conventional sing-around method using an external forced astable multivibrator in the sing-around circuit thereof, we have made extensive studies. As a result, a conclusion was reached that, because the frequency and the pulse width of a transmission pulse of said astable multivibrator cannot independently be adjusted, it is impossible to solve the aforementioned problems so long as said astable multivibrator is used for the sing-around method. The present invention has been made in view of the conclusion mentioned above.

More specifically, the apparatus of the present invention is characterized in that an asynchronous type one-shot pulse generator circuit is adopted in place of said external forced astable multivibrator causing synchronization with the frequency of an external synchronizing signal and also in that masking circuit and a pseudo-pulse generator circuit are provided to ensure smooth and certain continuation of sing-around actuation of a transmission pulse from said one-shot pulse generator circuit.

Now, the apparatus of the present invention is described in detail by way of examples with reference to the drawings.

EXAMPLE 1

FIG. 3 is a block diagram illustrating an embodiment of the apparatus of the present invention, and FIG. 5 is a graph illustrating the relation between a receiving signal and a transmission signal of the principal circuits in said embodiment.

In FIG. 3, 7 is a receiving probe for ultrasonic pulses, and 9 is a transmitting probe for transmitting ultrasonic pulses. Said receiving probe 7 and transmitting probe 9 forming a set are arranged opposite to each other obliquely at an angle on the outer surface of a pipe 8 so that an ultrasonic pulse may be emitted obliquely as shown by an arrow in the drawing to the flow direction of a liquid in the pipe 8 so as to avoid multiple reflection of an ultrasonic pulse. In the drawing, 10 is an amplifier which amplifies a signal from the receiving probe 7 to a magnitude sufficient to input into a masking circuit described later, as shown in FIG. 5 (a).

In FIG. 3, 11 is a masking circuit which transmits a masking signal as shown in FIG. 5 (c), in response to a normal signal (i) from the receiving probe 7 shown in FIG. 5 (a), which has been amplified by the amplifier 10. Said masking signal masks all of received waves (ii) having propagated along the wall of the pipe 8 and other noise waves (iii) shown in FIG. 5 (a) during a period from receiving of said normal signal (i) up to the moment immediately before receiving of the next normal signal (iv) from the receiving probe 7 (this period of time is hereafter referred to as the "masking time"), and also causes a one-shot pulse generator circuit described later to transmit a pulse. In other words, the masking circuit 11 has the function of preventing actuation of the one-shot pulse generator circuit described later, by noise signals other than the normal signal from the receiving probe 7. In FIG. 3, 12 is a masking time setup circuit which releases a masking signal of said masking circuit 11. More specifically, the masking time setup circuit 12 begins actuation upon resetting of the timer thereof by a pulse from the one-shot pulse generator circuit described later, and transmits a masking release signal to the masking circuit 11 upon the lapse of the preset time, i.e., the masking time. The masking time Tm shown in FIG. 5 (c) can be easily set at a desired value by a timer such as a preset counter. Said masking time Tm is set at a value which is slightly smaller than the sing-around period $T_1$ corresponding to a liquid flowing in the pipe 8 giving the highest sound velocity as shown in FIG. 5 (a) and which is sufficient to mask received noise waves such as (ii) and (iii) shown in FIG. 5 (a).

In FIG. 3, 13 is a one-shot pulse generator circuit which transmits a pulse as shown in FIG. 5 (b) in response to the masking signal from the masking circuit 11 as shown in FIG. 5 (c). Said pulse transmitted from said one-shot pulse generator circuit 13 serves also as a trigger signal to the masking time setup circuit 12, a receiving monitor-time setup circuit described later and a voltage/power converter circuit also described later.

In FIG. 3, 14 is a receiving monitor-time setup circuit and 16 is a pseudo-pulse generator circuit. When an ultrasonic pulse from the transmitting probe 9 has not been received by the receiving probe 7 within a preset time because of air bubbles or foreign matter entangled in the liquid flowing in the pipe 8, and this has interrupted pulses from the one-shot pulse generator circuit 13 as shown by a dotted line in FIG. 5 (b) and interrupted the normal sing-around actuation, the receiving monitor-time setup circuit 14 transmits a signal to the pseudo-pulse generator circuit 16 so as to cause said pseudo-pulse generator circuit 16 to transmit a pseudo-pulse as shown in FIG. 5 (d) to the masking circuit 11. The masking circuit 11 transmits a masking signal to the one-shot pulse generator circuit 13 in response to said pseudo-pulse as shown by an arrow in the drawing, and also carries out masking of noise signals. The one-shot pulse generator circuit 13 transmits a pulse in response to said masking signal as shown by another arrow in the drawing. Thus, the receiving monitor-time setup circuit 14 and the pseudo-pulse generator circuit 16 cause the interrupted sing-around actuation to resume immediately. More specifically, the receiving monitor-time setup circuit 14 begins actuation upon resetting of the timer thereof by a pulse from the one-shot pulse generator circuit 13. When said timer has not been reset again by the next pulse from the one-shot pulse generator circuit 13 within a preset time, i.e., a receiving monitor time, in other words, when an ultrasonic pulse from the transmitting probe 9 has not been received by the receiving probe 7 by some cause or other within the receiving monitor time, said receiving monitor-time setup circuit 14 transmits a signal to the pseudo-pulse generator circuit 16. The pseudo-pulse generator circuit 16 transmits a pseudo-pulse to the masking circuit 11 in response to said signal, and thus the sing-around actuation is continued without any trouble as mentioned above.

On the other hand, when the sing-around actuation is normal, and the timer of the receiving monitor-time setup circuit 14 has been reset again by the next pulse from the one-shot pulse generator circuit 13 within said receiving monitor time, only the next receiving monitor time is started, and the receiving monitor-time setup circuit 14 and the pseudo-pulse generator circuit 16 do not perform the above-mentioned actuation.

Said receiving monitor time can easily be set at a desired value by a timer such as a preset counter, and as shown in FIG. 5 (a), said receiving monitor time is set at a value slightly larger than the sing-around period $T_2$ corresponding to a liquid flowing in the pipe 8 giving the highest sound velocity.

The receiving monitor-time set up circuit 14 and the pseudo-pulse generator circuit 16 have also the function of causing the one-shot pulse generator circuit 13 to transmit the first pulse for starting the sing-around actuation when starting up the apparatus of the present invention.

In FIG. 3, 15 is a voltage/power converter circuit which converts a voltage signal from the one-shot pulse generator circuit 13 into a power signal and transmits said power signal to the transmitting probe 9. The transmitting probe 9 emits an ultrasonic pulse through the liquid flowing in the pipe 8 to the receiving probe 7 in response to said signal.

In FIG. 3, 17 is an abnormality detector circuit which counts the number of pseudo-pulses transmitted from the pseudo-pulse generator circuit 16 during a preset abnormality detecting time. When the number of counted pseudo-pulses has exceeded a preset value, i.e., when it has frequently happened that an ultrasonic pulse from the transmitting probe 9 has not been received in the normal manner by the receiving probe 7 by some cause or other, said abnormality detector circuit 17 deems such a state as an abnormality and transmits a signal to an alarm (not shown) to sound said alarm to awaken operators' attention, or transmits a signal to a device for taking action against the abnormality (not shown). Said abnormality detecting time and said preset number of pseudo-pulses can easily be set at desired values by a timer such as a preset counter. The aforementioned abnormality detector circuit is not indispensable for the apparatus of the present invention, but is to be provided as required.

In FIG. 3, 18 is an output section comprising a frequency/voltage converter and a recorder, which receives pulses transmitted in succession from the one-shot pulse generator circuit 13, i.e., sing-around frequency, and processes said received pulses in various manners for output. More specifically, said output section 18 converts said sing-around frequency into a voltage output by the frequency/voltage converter thereof and records said voltage output in the recorder thereof. When there occurs a change in the density of the liquid flowing in the pipe 8, i.e., when the boundary between different liquids passes a predermined point, this causes a change in the sing-around frequency, and hence a correspondingly change in the voltage output, thus resulting in a change in the indication of the recorder. It is therefore possible to detect the boundary between different liquids flowing in the pipe 8 from the change in the indication of the recorder of output section 18.

In FIG. 3, therefore, a pulse from the one-shot pulse generator circuit 13 is transmitted through the voltage/power converter circuit 15 to the transmitting probe 9. Said transmitting probe 9 transmits an ultrasonic pulse through the liquid flowing in the pipe 8 to the receiving probe 7 in response to said pulse. Said receiving probe 7 converts said ultrasonic pulse into a voltage signal. Said voltage signal is amplified by the amplifier 10 and then transmitted to the masking circuit 11. Said masking circuit 11 transmits a masking signal in response to said signal, and also performs masking of received noise waves. The one-shot pulse generator circuit 13 transmits a pulse in response to said masking signal. Normal sing-around actuation is thus continued.

On the other hand, said pulse from the one-shot pulse generator circuit 13 serves also as a trigger signal to the masking time setup circuit 12 and the receiving monitor-time setup circuit 14. More specifically, the masking time setup circuit 12 begins actuation in response to a pulse from the one-shot pulse generator circuit 13, and upon the lapse of a preset masking time, transmits a masking release signal to the masking circuit 11, thus setting up a masking time. The receiving monitor-time setup circuit 14 begins actuation in response to a pulse from the one-shot pulse generator circuit 13. When normal sing-around actuation has been interrupted by some cause or other during a preset receiving monitor time, the receiving monitor-time setup circuit 14 transmits a signal to the pseudo-pulse generator circuit 16, and causes said pseudo-pulse generator circuit 16 to transmit a pseudo-pulse to the masking circuit 11, thus enabling the sing-around actuation to be continued. Furthermore, an abnormality detector circuit 17 is provided to sound an alarm (not shown) when it frequently happens that sing-around actuation is interrupted.

EXAMPLE 2

Figure 4:
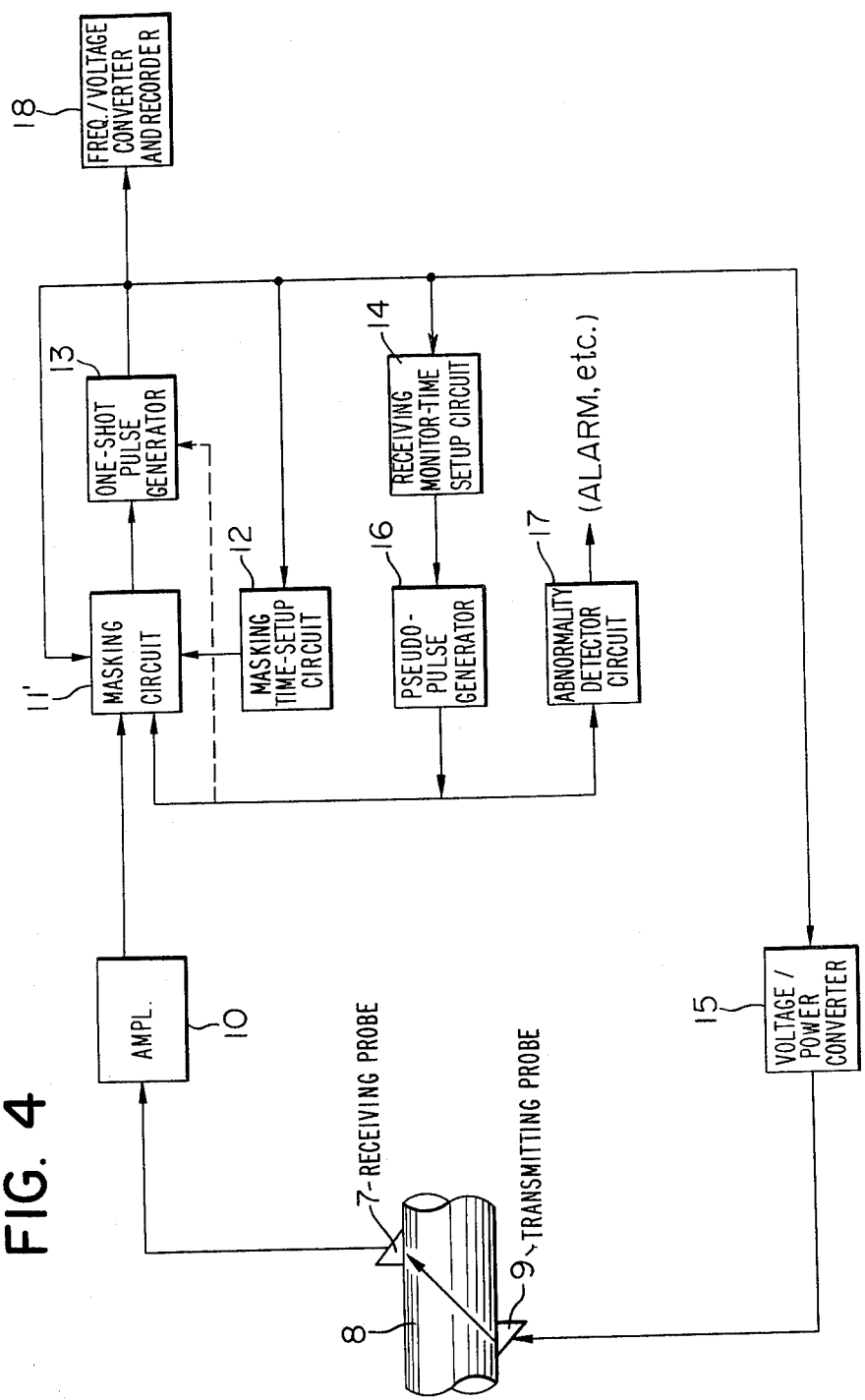
FIG. 4 is a block diagram illustrating another embodiment of the apparatus for detecting a change in parameters of a liquid flowing in a pipe based on the sing-around method, of the present invention.

FIG. 4 is a block diagram illustrating another embodiment of the apparatus of the present invention. In FIG. 4, the same reference numerals as in FIG. 3 indicate the same components as in FIG. 3.

In FIG. 4, 11' is a masking circuit. The masking circuit 11' has slightly different construction and actuation from the masking circuit 11 described in Example 1 above. More specifically, the masking circuit 11' causes a signal from the receiving probe 7, which has been amplified by the amplifier 10, to pass the masking circuit 11' without causing any masking actuation and directly reach the one-shot pulse generator circuit 13. The one-shot pulse generating circuit 13 transmits a pulse to the masking circuit 11' in response to said signal. The masking circuit 11' transmits a masking signal in response to said pulse from the one-shot pulse generator circuit 13 and at the same time begins masking.

The masking circuit 11 in Example 1 (FIG. 3) begins masking in response to a signal from the receiving probe 7 and at the same time causes the one-shot pulse generator circuit 13 to transmit a pulse, whereas the masking circuit 11' in Example 2 (FIG. 4) begins masking not by a signal from the receiving probe 7, but by a pulse from the one-shot pulse generator circuit 13. A pulse from the one-shot pulse generator circuit 13 in Example 2 (FIG. 4) serves also as a trigger signal to the masking time setup circuit 12, the receiving monitor-time setup circuit 14 and the voltage/power converter circuit 15, just as in Example 1.

When employing the above-mentioned masking circuit 11', a pseudo-pulse from the pseudo-pulse generator circuit 16 may be directly transmitted to the one-shot pulse generator circuit 13 in place of the masking circuit 11', as shown by a dotted line in FIG. 4.

The described apparatus of the present invention is for detecting the boundary between different liquids flowing in a pipe both in Examples 1 and 2 mentioned above. However, the apparatus of the present invention is not limited to the detection of said boundary between different liquids. It is also applicable for the detection of a change in parameters such as the bulk modulus, the concentration and the temperature of a liquid flowing in a pipe.

By using the apparatus of the present invention, as described above in detail, it is possible to easily adjust the masking time and the receiving monitor time to desired values. According to the present invention, therefore, the following industrially useful effects are provided:

(1) A simple adjustment permits application of the apparatus of the present invention to a pipe of a different diameter.

(2) In the apparatus of the present invention, which permits extension of the masking time to the extent not impairing receiving of normal signals from the transmitting probe, it is possible to substantially eliminate received noise waves.

(3) In the apparatus of the present invention, even when normal sing-around actuation has been interrupted by some cause or other, it is possible to continue automatically and immediately sing-around actuation by setting up the receiving monitor time at an appropriate value.

(4) In the apparatus of the present invention, when it frequently happens that normal sing-around actuation is interrupted, it is possible to know the occurrence of such an abnormality through an alarm automatically sounded by adding an abnormality detector circuit.

What is claimed is:

1. An apparatus for detecting a change in parameters of a liquid flowing in a pipe based on the sing-around method, which comprises:

a set of a transmitting probe and a receiving probe arranged opposite to each other on the outer surface of a pipe, said transmitting probe emitting an ultrasonic pulse through a liquid flowing in said pipe to said receiving probe, and said receiving probe converting said ultrasonic pulse from said transmitting probe into a voltage signal and transmitting said voltage signal;

an amplifier for amplifying said voltage signal from said receiving probe;

a masking circuit for transmitting a masking signal in response to said signal from said receiving probe as amplified by said amplifier, said masking circuit masking, during a preset masking time, noise signals other than normal ones from among signals from said receiving probe;

a one-shot pulse generator circuit for transmitting a pulse in response to said making signal from said masking circuit;

a masking time setup circuit for setting up said masking time, said masking time setup circuit beginning actuation immediately upon resetting of a timer thereof in response to said pulse from said one-shot pulse generator circuit, and releasing said masking by said masking circuit by transmitting a masking release signal to said masking circuit at the moment when said masking time has elapsed, and said masking time being set up at a desired value by said timer within a range of periods slightly smaller than the sing-around period corresponding to a liquid flowing in said pipe giving the highest sound velocity and sufficient to permit masking of said noise signals;

a receiving monitor-time setup circuit for setting up a receiving monitor time during which interruptions of pulses transmitted from said one-shot pulse generator circuit are monitored, said receiving monitor-time setup circuit beginning actuation immediately upon resetting of a timer thereof in response to said pulse from said one-shot pulse generator circuit, and transmitting a signal when said timer has not been reset again by the next pulse from said one-shot pulse generator circuit during said receiving monitor time, and said receiving monitor time being setup by said timer at a desired value slightly larger than the sing-around period corresponding to a liquid flowing in said pipe giving the lowest sound velocity;

a pseudo-pulse generator circuit for transmitting a pseudo-pulse to said masking circuit in response to said signal from said receiving monitor-time setup circuit, said pseudo-pulse, like said signal from said receiving probe, causing said masking circuit to transmit a masking signal in response to said pseudo-pulse;

a voltage/power converter circuit for converting said pulse from said one-shot pulse generator circuit into a power signal and transmitting said power signal to said transmitting probe, said transmitting probe transmitting the next ultrasonic pulse in response to said power signal, and thus the sing-around actuation being continued; and an output section for taking out a pulse from said one-shot pulse generator circuit as an output, said output section comprising a frequency/voltage converter circuit and a recorder.

2. The apparatus as claimed in claim 1, wherein said masking circuit is adapted to cause said signal from said receiving probe to pass said masking circuit without causing any masking actuation to reach directly said one-shot pulse generator circuit and to cause said one-shot pulse generator circuit to transmit a pulse, and wherein said masking circuit includes means for transmitting a masking signal in response to said pulse from said one-shot pulse generator circuit.

3. The apparatus as claimed in claim 2, wherein said pseudo-pulse generator circuit is adapted to transmit said pseudo-pulse directly to said one-shot pulse generator circuit in place of said masking circuit.

4. The apparatus as claimed in claim 3, further comprising an abnormality detector circuit, said abnormality detecting circuit including means for counting the number of said pseudo-pulses transmitted from said pseudo-pulse generator circuit during a preset period of time, and for transmitting a signal when said counted number of pseudo-pulses has exceeded a preset value.

5. The apparatus as claimed in claim 2, further comprising an abnormality detector circuit, said abnormality detecting circuit including means for counting the number of said pseudo-pulses transmitted from said pseudo-pulse generator circuit during a preset period of time, and for transmitting a signal when said counted number of pseudo-pulses has exceeded a preset value.

6. The apparatus as claimed in claim 1, further comprising an abnormality detector circuit, said abnormality detecting circuit including means for counting the number of said pseudo-pulses transmitted from said pseudo-pulse generator circuit during a preset period of time, and for transmitting a signal when said counted number of pseudo-pulses has exceeded a preset value.

* * * * *